United States Patent
Baek et al.

(10) Patent No.: US 9,439,970 B2
(45) Date of Patent: Sep. 13, 2016

(54) SOLID DISPERSIONS OF INSOLUBLE DRUG AND PREPARATION METHOD THEREOF

(71) Applicant: SK BIOPHARMACEUTICALS CO., LTD., Seoul (KR)

(72) Inventors: Myoung Ki Baek, Daejeon (KR); Augustin Pegan, South Fair Lawn, NJ (US)

(73) Assignee: SK BIOPHARMACEUTICALS CO., LTD., Seoul (KR)

( * ) Notice: Subject to any disclaimer, the term of this patent is extended or adjusted under 35 U.S.C. 154(b) by 0 days.

(21) Appl. No.: 14/441,277

(22) PCT Filed: Nov. 7, 2013

(86) PCT No.: PCT/KR2013/010088
§ 371 (c)(1),
(2) Date: May 7, 2015

(87) PCT Pub. No.: WO2014/073889
PCT Pub. Date: May 15, 2014

(65) Prior Publication Data
US 2015/0283243 A1    Oct. 8, 2015

(30) Foreign Application Priority Data

Nov. 7, 2012   (KR) .................. 10-2012-0125516

(51) Int. Cl.
| | |
|---|---|
| *A61K 47/32* | (2006.01) |
| *A61K 31/42* | (2006.01) |
| *C07D 261/08* | (2006.01) |

(Continued)

(52) U.S. Cl.
CPC ............. *A61K 47/32* (2013.01); *A61K 9/10* (2013.01); *A61K 9/146* (2013.01); *A61K 31/42* (2013.01); *C07D 261/08* (2013.01); *A61K 9/2027* (2013.01)

(58) Field of Classification Search
None
See application file for complete search history.

(56) References Cited

U.S. PATENT DOCUMENTS

| | | | |
|---|---|---|---|
| 5,811,547 A | 9/1998 | Nakamichi et al. | .......... 540/589 |
| 2011/0301150 A1* | 12/2011 | Park | .......... A61K 31/16 514/218 |
| 2013/0046001 A1* | 2/2013 | Park | .......... A61K 31/4196 514/378 |

FOREIGN PATENT DOCUMENTS

| | | | | |
|---|---|---|---|---|
| KR | 10-2010-0097059 | | 9/2010 | ........... C07D 249/10 |
| KR | 10-2011-0121919 | | 11/2011 | ........ A61K 31/4196 |

(Continued)

OTHER PUBLICATIONS

Kirk-Othmer Encyclopedia of Chemical Technology Copyright © 2002 by John Wiley & Sons, Inc., pp. 95-147, Article Online Posting Date: Aug. 16, 2002.*

(Continued)

*Primary Examiner* — Karl J Puttlitz
(74) *Attorney, Agent, or Firm* — Harness, Dickey & Pierce, P.L.C.

(57) ABSTRACT

The present invention relates to a solid dispersion characterized in that it comprises carbamic acid 3-(4-benzyloxyphenyl)-isoxazol-5-ylmethyl ester as an active ingredient and a water-soluble polymer having a glass transition temperature lower than the melting point of the active ingredient as a carrier, and it is prepared via melt extrusion. The solid dispersion of the present invention remarkably increases the solubility and dissolution rate of the active ingredient which is an insoluble drug to efficiently improve the bioavailability when it is orally administered.

9 Claims, 3 Drawing Sheets

(51) Int. Cl.
*A61K 9/14* (2006.01)
*A61K 9/10* (2006.01)
*A61K 9/20* (2006.01)

(56) References Cited

FOREIGN PATENT DOCUMENTS

| WO | WO 92/18106 | 10/1992 | ............... A61K 9/14 |
|----|-------------|---------|---------------------------|
| WO | 93/11749 | * 6/1993 | |
| WO | WO 93/11749 | 6/1993 | ............... A61K 9/10 |
| WO | WO 2012/122279 | 9/2012 | ............. A61K 31/54 |

OTHER PUBLICATIONS

Ullmann's Encyclopedia of Industrial Chemistry, Copyright © 2002 by Wiley-VCH Verlag GmbH & Co. KGaA , pp. 1-51.*
Rouhi, "The Right Stuff, from research and development to the clinic, getting drug crystals right is full of pitfalls", Chemical & Engineering News, Feb. 24, 2003, pp. 32-35.*
Vitamin E TPGS NF and Food Grade, Jun. 20012.*
International Search Report (ISR) dated Feb. 20, 2014 in PCT/KR2013/010088 published as WO 2014/073889.

* cited by examiner

SOLID DISPERSIONS OF INSOLUBLE DRUG AND PREPARATION METHOD THEREOF

CROSS-REFERENCE TO RELATED APPLICATIONS

This application is a national phase application of PCT Application No. PCT/KR2013/010088, filed on 7 Nov. 2013, which claims benefit of Korean Patent Application 10-2012-0125516, filed on 7 Nov. 2012. The entire disclosure of the application identified in this paragraph is incorporated herein by reference.

TECHNICAL FIELD

The present invention relates to a solid dispersion that can be used for improving bioavailability of an insoluble drug when it is orally administered, particularly a solid dispersion of the insoluble drug, carbamic acid 3-(4-benzyloxy-phenyl)-isoxazol-5-ylmethyl ester, and a preparation method thereof.

BACKGROUND ART

Carbamic acid 3-(4-benzyloxy-phenyl)-isoxazol-5-ylmethyl ester is an azole derivative having the following formula:

It was filed as Korean Patent Application No. 2010-0016686. This compound has a high protection efficacy for the nerve cell and thus shows a therapeutic effect to such diseases associated with the death of nerve cells or neurodegeneration. However, since it has an extremely low solubility in water, it shows a very low bioavailability when orally administered.

Insoluble drugs show a low solubility and dissolution rate in the gastric juice, body fluids, etc. due to their low solubility in water and thus their absorption through the gastrointestinal tract is inhibited to give a low bioavailability when they are orally administered. Thus, various approaches have been tried to improve the solubility or absorptivity of the insoluble drugs. Examples thereof include converting the crystalline compound to its amorphous form, giving the physical change of increasing the surface area through micronization, or developing an emulsion or a microemulsion using a surfactant or a suitable solvent to increase the solubility and absorptivity. Since the amorphous form has a higher water solubility—as much as 10-1600 times or more than the crystal form—if a compound is converted to an amorphous form, its bioavailability may increase remarkably. However, the amorphous form is highly apt to be recrystallized again to a crystal form having a low free energy with the passage of time and thus has the disadvantage of low storage stability. The approach of increasing surface area through the micronization of particles may be effective in improving the solubility rate of such compounds having a low solubility rate. However, the intrinsic solubility of a compound cannot be changed. Furthermore, the micronization using a mill such as a hammer mill or a jet mill can be applied with some limitation depending on the energy reactivity of the compound. Methods for improving solubility by preparing a microemulsion using a solubilizer such as a surfactant are frequently applied, but the use of a solubilizing agent, organic solvent or surfactant is constrained due to their toxicity. As another method for improving the solubility of insoluble drugs, researches using a solid dispersion have been tried. The solid dispersion is a system wherein the drug particles are dispersed in the water-soluble polymer matrix in the solid phase. It can broaden the surface area of drug particles by reducing their size. Since the drug is converted to an amorphous form during the method of preparing the solid dispersion and thus exists partially or completely in amorphous form, it is effective in terms of increasing the drug solubility and its storage property. Spray-drying and melt-extrusion have been known as methods for preparing the solid dispersion. Spray-drying is a method for preparing the solid dispersion by mixing a drug and a water-soluble polymer with a suitable solvent depending on the characteristics of the drug and the water-soluble polymer, and then spraying the mixture. The spray-drying method has the problem that it is difficult to find a solvent that can dissolve the insoluble drug and the water-soluble polymer together. Particularly, when the drug has a low solubility in the solvent selected, since a large amount of the organic solvent should be used, the method can hardly be applied in commercial production and may cause the problems of solvent recovery and environmental pollution. The melt-extrusion is a method for forming solid dispersion by melting a mixture of drug and water-soluble polymer at the temperature of the melting point of the drug and the glass transition temperature of the polymer mixture or higher to convert the drug into an amorphous form and by extruding it, endowing the polymer with plasticity. The present inventors have found that a solid dispersion of an insoluble compound, whose solubility, bioavailability and physicochemical stability are remarkably improved, can be effectively prepared by using the melt-extrusion method under specific conditions. They then completed the present invention.

CITED PRIOR ART

Patent Documents

Korean Patent Application No. 2010-0016686
Korean Patent Application No. 2010-0041436

DISCLOSURE OF INVENTION

Technical Problem

The present invention provides a solid dispersion that can improve the solubility and physico-chemical stability of the insoluble drug, carbamic acid 3-(4-benzyloxy-phenyl)-isoxazol-5-ylmethyl ester compound, and a preparation method thereof.

Solution to Problem

In order to solve the problem, the present invention provides a solid dispersion characterized in that it comprises carbamic acid 3-(4-benzyloxy-phenyl)-isoxazol-5-ylmethyl ester as an active ingredient and a water-soluble polymer having the glass-transition temperature lower than the melting point of carbamic acid 3-(4-benzyloxy-phenyl)-isoxazol-5-ylmethyl ester as a carrier, and it is prepared via melt extrusion. The solid dispersion of the present invention may further comprise a plasticizer.

The present invention also provides a method for preparing the solid dispersion by mixing the active ingredient carbamic acid 3-(4-benzyloxy-phenyl)-isoxazol-5-ylmethyl ester with the carrier water-soluble polymer and by melt-extruding this mixture at a temperature lower than the melting point of the active ingredient. In the method according to the present invention, the mixture may further comprise a plasticizer.

Hereinafter, the present invention will be explained in greater detail.

The active ingredient carbamic acid 3-(4-benzyloxy-phenyl)-isoxazol-5-ylmethyl ester ("CBI," below) used in the present invention is a substituted azole derivative having the following formula. In the present invention, the term CBI is used as comprising all the pharmaceutically acceptable salts, isomers, solvates and combinations thereof.

CBI may be used for the purpose of prevention or treatment of diseases selected from the group consisting of ictus, Alzheimer's disease, Huntington's disease, Parkinson's disease, Pick's disease, Creutzfeld-Jacob disease, Parkinson-ALS-dementia complex of Guam, Wilson's disease, multiple sclerosis, progressive supranuclear palsy, neuropathic pain and bipolar disorder, corticobasal degeneration, schizophrenia, attention deficit hyperactivity disorder, dementia, amyotrophic lateral sclerosis, retinal disease, epilepsy, stroke, transient ischemic attacks, myocardial ischemia, myoischemia, ischemia caused by surgical technique associated with the extended stoppage of cerebral blood flow, head trauma, spinal cord trauma, hypoxia and depression.

The above active ingredient CBI is contained preferably in the amount of 10 to 70 wt % based on the total weight of the composition. It is easy to secure the content homogeneity in the solid dispersion when the active ingredient is contained in the amount of at least 10 wt %, and the effect of improved bioavailability and the solubilization due to the mixing with the polymer carrier can be achieved when the active ingredient is contained in the amount of 70 wt % or less.

In the solid dispersion of the present invention, the carrier may include a water-soluble polymer having a glass transition temperature lower than that of the active ingredient CBI, preferably polyvinyl pyrrolidone and/or hypromellose acetate succinate, more preferably polyvinyl pyrrolidone K30 as the polyvinyl pyrrolidone. The water-soluble polymer is contained preferably in the amount of 30 wt % or more, more preferably in the amount of 30 to 90 wt %, based on the total weight of the composition. Polyvinyl pyrrolidone having any molecular weight can be used, but in particular those having the molecular weight of 30,000 to 60,000 are desired since they may build the viscosity which is easy for melt-extrusion.

The present invention may comprise a plasticizer. Any plasticizer that can facilitate the melt-molding can be used, but D-alpha-tocopheryl polyethylene glycol 1000 succinate (TPGS), polyethylene glycol 400 or both of them can be preferably used. The plasticizer is used preferably in the amount of 1 to 10 wt % based on the total weight of the composition.

As preferable embodiments of the present invention, there are provided solid dispersions comprising the active ingredient CBI in 10 to 50 wt % and the water-soluble polymer polyvinyl pyrrolidone in 50 to 90 wt %, or comprising the active ingredient CBI in 10 to 50 wt %, the water-soluble polymer polyvinyl pyrrolidone or hypromellose acetate succinate in 45 to 85 wt % and the plasticizer D-alpha-tocopheryl polyethylene glycol 1000 succinate (TPGS) or polyethylene glycol 400 in 1 to 5 wt %.

The present invention also provides a method for preparing the CBI-containing solid dispersion by mixing CBI, a water-soluble polymer and an optional plasticizer, and by melt-extruding this mixture at a temperature lower than the melting point of CBI. In particular, the method of the present invention is characterized in that the solid dispersion is prepared by melt-extruding at a temperature lower than the melting point of the active ingredient CBI.

The above mixture is melted when it passes through four (4) or more heating blocks whose temperature is sequentially lowered. Specifically, the mixture of drug and water-soluble polymer which have been mixed in advance as a powder is introduced into an extruder and melt-extruded to prepare the solid dispersion of the present invention wherein the extruder is made of several heating blocks designed to be distinguished from each other and which are connected in series. Here, the distinguished heating blocks are controlled to have a temperature lower than the melting point of the melted drug—i.e., the active ingredient CBI. More preferably, the heating blocks consist of the first to fourth heating blocks wherein the melting temperature of the first heating block is controlled to 160 to 145° C., that of the second heating block to 144 to 120° C., that of the third heating block to 119 to 80° C., and that of the fourth heating block to 79 to 70° C.

From the earlier method of preparing a solid dispersion by melt-extruding at a temperature which is conventionally higher—as much as, for example, 15 to 30° C. or more—than the melting point of a drug for the complete conversion of the drug to an amorphous form, the preparation method of the present invention is different in that a solid dispersion is prepared by melt-extruding at a temperature lower than the melting point of the active ingredient CBI. Although the melting is performed at a temperature lower than the melting point, the extrusion is performed through the specific sustained cooling and sequential melting by passing through the several heating blocks whose setting temperatures are lowered sequentially. Thereby, the active ingredient is sufficiently converted to an amorphous form even at a temperature lower than the melting point, and it is possible to prepare the solid dispersion showing an excellent dissolution pattern and bioavailability as illustrated in Table 13, and FIGS. 2 and 3. As explained above, since the solid dispersion is prepared by melt-extruding at a temperature lower than the melting point of the active ingredient CBI in the preparation method of the present invention, there is no possibility of decomposition or damage of the active ingredient CBI or the carrier polymer used. Also, since the use of an organic solvent is not required for preparing the dispersion, there is no concern about environmental pollution or endangering the working environment. The solid dispersion prepared according to the present invention or the oral preparation comprising the solid dispersion does not comprise any organic solvent, surfactant, etc. but comprises only the water-soluble polymer which is very safe in the body, and thus it is very excellent in terms of safety. Furthermore, in comparison to the spray-drying method, the preparation method does not need the step of selecting an organic solvent and thus is simple.

The solid dispersion according to the present invention is extruded as a solid and may be solidified in the form of a long capillary. It is pulverized by using a suitable cutter or pulverizer so that it may be prepared in the form of a powder. This powder may be formulated in the form of a tablet capable of being administered into the human body or filled into a gelatin capsule.

When the solid dispersion is formulated as an oral preparation for the convenience of administration, it may comprise a pharmaceutically acceptable excipient. As the excipient, microcrystalline cellulose or lactose may be used as a diluent for achieving the desired volume, and magnesium stearate, stearic acid or $SiO_2$ may be added as a lubricant for endowing the powder with fluidity and preventing mechanical adhesion during filling of the capsule. Also, as a disintegrating agent for assisting the disintegration of a tablet, croscarmellose sodium, sodium starch glycolate and crospovidone may be used.

The solid dispersion according to the present invention conspicuously increases solubility of the insoluble compound CBI in water. Thereby CBI shows a dissolution rate that satisfies the criteria of the Dissolution Test of Tablet (see Experiment 3). Also, as a result of a pharmacokinetic test using Beagle dogs, the dispersion shows the superior bioavailability to CBI after its oral administration (see Experiment 4).

Thus, the composition for oral administration and the pharmaceutical composition, each of which comprises the solid dispersion of the present invention, can be effectively used for the treatment of the above-stated diseases, against which CBI exhibits a therapeutic efficacy, in particular the diseases of central nervous system including degenerative brain disease.

Hereinafter, the present invention will be explained more in detail by the Examples. However, the following Examples are only for the illustration of the present invention as specific types of techniques in the practice thereof, and it is not intended that the scope of the present invention would be limited in any manner by them.

Advantageous Effects of Invention

The solid dispersion of the present invention remarkably increases the solubility and dissolution rate of the insoluble compound CBI to efficiently improve bioavailability when it is orally administered. The preparations containing the solid dispersion of the present invention are physico-chemically very stable and have high storage stability. Furthermore, since the method for preparing the solid dispersion according to the present invention uses neither an organic solvent nor a surfactant, it is safe. The dispersion is melt-extruded at a temperature lower than the melting point of the active ingredient, and thus there is no worry about decomposition or damage of the active drug or polymer, and the preparation method is simple.

BEST MODE FOR CARRYING OUT THE INVENTION

Preparation 1

Preparation of carbamic acid 3-(4-benzyloxy-phenyl)-isoxazol-5-ylmethyl ester (CBI)

The preparation of carbamic acid 3-(4-benzyloxy-phenyl)-isoxazol-5-ylmethyl ester (CBI) is described in detail in Korean Patent Application No. 2010-0041436. Specifically, it was prepared as follows.

4-Benzyloxybenzaldehyde (4.24 g, 20 mmol) was dissolved in a solvent mixture of ethanol and water (3:1, 100 ml) in the concentration of 0.2 M while stirring. $NH_2OH$—HCl (2.78 g, 40 mmol) and sodium acetate (2.46 g, 30 mmol) were added thereto, which was then stirred for about 30 min at room temperature. The completion of reaction was confirmed by liquid chromatography, and water and ethanol were distilled off under reduced pressure to give a pale yellow solid compound. This solid compound was extracted three times with water and ethyl acetate, and the organic solvent layer was subjected to the condition of reduced pressure. The crude compound was recrystallized from hexane/ethyl acetate (10:1) to give a compound as a white solid. Thus obtained solid 4-benzyloxy-benzaldehydeoxime (2.27 g, 10 mmol; a compound of 92% purity) was dissolved in methylene chloride (40 ml, 0.25 M), and propargyl alcohol (1.77 ml, 30 mmol) was added thereto. To this solution was very slowly added in drops 10% NaOCl (13.7 ml, 20 mmol) at 0° C. by using a dropping funnel. After all NaOCl was added, the mixture was stirred for about 5 h during which the temperature was slowly raised to room temperature. After the completion of reaction was confirmed by liquid chromatography, the reaction mixture was distilled under reduced pressure to evaporate methylene chloride. Water (200 ml) was added to the residue, and the resulting solid was filtered. The compound thus filtered was washed with excess water and then finally washed with diethyl ether. The solid compound thus obtained was recrystallized from ethyl acetate/hexane (1:2) to give [3-(4-benzyloxy-phenyl)-isoxazol-5-yl]-methanol as a white solid (Yield: 2.5 g). Chlorosulfonyl isocyanate (1.04 ml, 12 mmol) was slowly added to the THF solution (50 ml, 0.2 M) containing [3-(4-benzyloxy-phenyl)-isoxazol-5-yl]-methanol (2.813 g, 10 mmol) in a 250 ml flask at −78° C. After disappearance of all the starting materials was confirmed by liquid chromatography, water was added to the reaction solution. After 1 h, distillation under reduced pressure was carried out to evaporate THF. Water (100 ml) was added thereto, and the resulting solid was filtered. Thus filtered solid was washed with 100 me of water and ethyl acetate/hexane (1:2) solution, and dried to give 3.4 g of the crude product (Purity: 95.9%). This crude product was recrystallized from ethyl acetate/hexane/methylene chloride (1:4:1) solution containing 1% methanol to give 2.743 g of carbamic acid 3-(4-benzyloxy-phenyl)-isoxazol-5-ylmethyl ester (CBI) in the purity of 99%.

Examples 1 to 6

Preparation of Melt-Extruded Solid Dispersions

Figure 1:
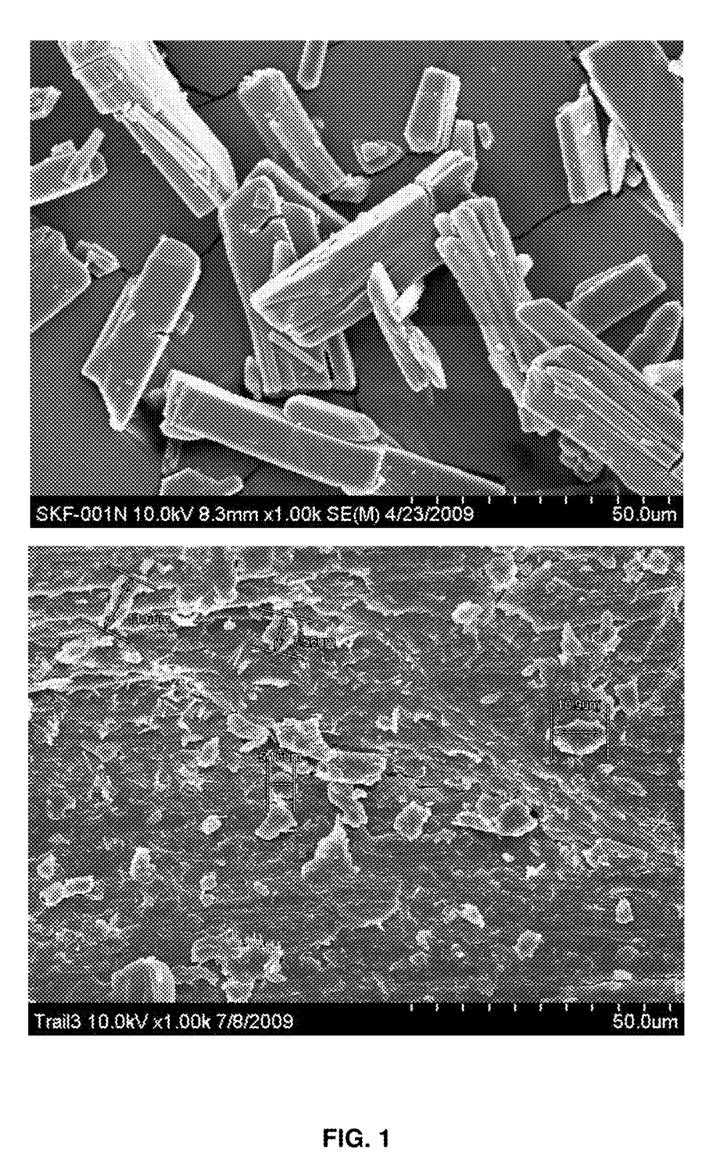
FIG. 1 shows the results by Scanning Electron Microscopy for CBI obtained in Preparation 1 (left) and the CBI-containing solid dispersion of the present invention obtained in Example 1 (right).

Solid dispersions having the compositions of Tables 2 to 7 were prepared from a mixture of CBI, a water-soluble polymer and a plasticizer by using a twin screw having an 18 mm diameter. The mixtures were introduced into an extruder wherein four distinguished heating blocks (Zone 1~Zone 4) were connected in series, and the solid dispersions obtained by melt-mixing and extruding were pulverized by a pulverizer to give the solid dispersions of Examples 1 to 6 as a powder. The detailed preparation condition is shown in Table 1. Polyvinylpyrrolidone PVP K30 was used as the water-soluble polymer. A photograph was taken of the CBI obtained in Preparation 1 (left) and the CBI-containing solid dispersion obtained in Example 1 (right) by Scanning Electron Microscopy as shown in FIG. 1. As can be seen from FIG. 1, in the solid dispersion CBI is uniformly dispersed in the polymer matrix mainly in the form of amorphous microstructure.

TABLE 1

| Parameter | Result |
| --- | --- |
| Extruder | Leistritz 18-mm |
| Screw Speed | 250 rpm |
| Die | Single Bore, Round, 3.0 mm diameter |
| Zone 4 Temperature | 75° C. |
| Zone 3 Temperature | 110° C. |
| Zone 2 Temperature | 140° C. |
| Zone 1 Temperature | 150° C. |
| Feed Speed of Powder | 1.0 kg/hr |
| Feeder Screw | 20 mm single flight screw |
| Pulverizer | Fitzmill L1A |
| Pulverising Rate | 9,000 rpm |
| Standard Sieve | 20 |

TABLE 2

| Ingredient | Final Composition Ratio (wt %) |
| --- | --- |
| CBI | 15% |
| Polyvinylpyrrolidone | 85% |

TABLE 3

| Ingredient | Final Composition Ratio (wt %) |
| --- | --- |
| CBI | 30% |
| Polyvinylpyrrolidone | 70% |

TABLE 4

| Ingredient | Final Composition Ratio (wt %) |
| --- | --- |
| CBI | 30% |
| Polyvinylpyrrolidone | 69% |
| TPGS | 1% |

TABLE 5

| Ingredient | Final Composition Ratio (wt %) |
| --- | --- |
| CBI | 30% |
| Polyvinylpyrrolidone | 69% |
| Polyethylene glycol 400 | 1% |

TABLE 6

| Ingredient | Final Composition Ratio (wt %) |
| --- | --- |
| CBI | 15% |
| Hypromellose acetate succinate | 84% |
| Polyethylene glycol 400 | 1% |

TABLE 7

| Ingredient | Final Composition Ratio (wt %) |
| --- | --- |
| CBI | 50% |
| Hypromellose acetate succinate | 40% |
| TPGS | 10% |

Comparative Example 1

Preparation of Melt-Extruded Solid Dispersion

The melt-extruded solid dispersion of Comparative Example 1 was prepared according to the same procedure as Example 1 except that the temperatures of heating blocks were set up as follows. Impurities were measured by using the high-performance liquid chromatography for the solid dispersions of Example 1 and Comparative Example 1. The column used in the present experiment was a 150 cm×4.6 mm, 3.5 μm C18 column, the flow rate was 1.0 mL/min, the column temperature was 30° C., and the detection was performed at 260 nm. The mobile phase was applied for 30 min under the following gradient condition with acetonitrile and 0.1% aqueous trifluoroacetic acid solution.

TABLE 8

| Time (Min) | Acetonitrile | 0.1% Aqueous trifluoroacetic acid solution |
| --- | --- | --- |
| 0 Min | 45 | 55 |
| 12 Min | 45 | 55 |
| 20 Min | 80 | 20 |
| 22 Min | 45 | 55 |
| 30 Min | 45 | 55 |

As a result, in the case of the solid dispersion of Comparative Example 1 which was obtained by warming and melting in Zone 1 whose initial temperature was the melting point of CBI, decomposition products were generated during the procedure and impurities corresponding to the Relative Retention Times (RRTs) of 0.87 and 1.32, the total amount thereof being 6.5%, were detected. However, the total impurity of only 0.6% was detected in the solid dispersion of the present invention. From this result, it was confirmed that the preparation method of the present invention is a safe method wherein the active ingredient is hardly decomposed.

TABLE 9

| Heating Block | Comparative Example - Condition 1 |
|---|---|
| Zone 1 | 165 |
| Zone 2 | 155 |
| Zone 3 | 140 |
| Zone 4 | 90 |
| CBI Content (%) | 93.5% |
| Total Impurity (%) | 6.5% |

Example 7

Preparation of the Solid Dispersion-Containing Tablet

The solid dispersion thus prepared may be formulated into a tablet for the purpose of easy administration. The tablet was prepared by adding the pharmaceutically acceptable disintegrating agent, diluent and lubricant as excipients needed for the preparation of a tablet. Specifically, the solid dispersion obtained in Example 2, croscarmellose sodium as a disintegrating agent, magnesium stearate as a lubricant and microcrystalline cellulose as a diluent were used. The tablet was prepared by using $SiO_2$ for the purpose of increasing fluidity, and the amounts of ingredients are shown in the following Table 10.

TABLE 10

| Ingredient | Unit Weight (mg) | Ratio (%) | Function |
|---|---|---|---|
| CBI solid dispersion of Example 2 | 16.7 | 6.7 | Main ingredient Solid dispersion (CBI 30%, water-soluble polymer 70%) |
| Microcrystalline Cellulose (Avicel PH102) | 217.1 | 86.8 | Diluent |
| Croscarmellose Sodium (Ac-Di-Sol) | 12.5 | 5 | Disintegrating Agent |
| Magnesium Stearate | 1.25 | 0.5 | Lubricant |
| $SiO_2$ | 2.5 | 1 | Fluidizer |
| Total Amount | 250 | 100 | |

Experiment 1

Identification of Solubility of the Active Ingredient CBI

Under several solvent conditions—i.e., distilled water, methanol, ethanol, acetone and diethyl ether—the solubility of CBI was measured. Specifically, about 5 to 40 mg of CBI was introduced into a 1.5 mL microtube, and 1 mL of the test solvent was added thereto. The mixture was slowly stirred in a rotary stirrer for 24 h under the condition of room temperature until solvent equilibrium was reached. After stirring, the suspended solution was filtered through a 0.45 micrometer membrane filter. The supernatant was collected and diluted by two-fold with the same amount of diluent for analysis. The CBI concentration was analyzed by using high-performance liquid chromatography. The column used in the present experiment was a 150 cm×4.6 mm, 5 μm C18 column, and the mobile phase was a mixture of 35% acetonitrile, 20% methanol and 45% distilled water by volume. The flow rate was 1.0 mL/min, and the detection was performed at 255 nm. The results are shown in Table 11 wherein the values are represented as an average of three repeats±standard deviation.

TABLE 11

| Solvent | Solubility (mg/mL) |
|---|---|
| Distilled Water | Not detected |
| Methanol | 2.5 |
| Ethanol | 1.5 |
| Diethyl Ether | 0.7 |
| Acetone | 24.8 |

From the above results, it is confirmed that CBI is an extremely insoluble compound that is hardly dissolved in water.

Experiment 2

Thermal Analysis of CBI

Evaluations of melting point and heat-dependent change of characteristics of CBI were performed by DSC (Differential Scanning calorimetry). The experimental procedure was briefly explained below. 1 to 2 mg of CBI weighed accurately and was introduced into a standard aluminum pan. The temperature was raised from 50° C. to 350° C. at the heating rate of 100° C./min. The thermal characteristics were analyzed under the nitrogen stream of 25 mL/min. The analysis results are shown in Table 12.

TABLE 12

| | Melting Point (° C.) | | |
|---|---|---|---|
| Sample No. | Starting Temperature | Peak Time | Heat of Fusion Δ H (J/g) |
| First | 164.15 | 167.94 | 155.692 |
| Second | 164.23 | 167.09 | 129.708 |
| Average | 164.19 | 167.52 | 142.700 |

Experiment 3

Dissolution Test of the Solid Dispersion-Containing Tablet

Figure 2:
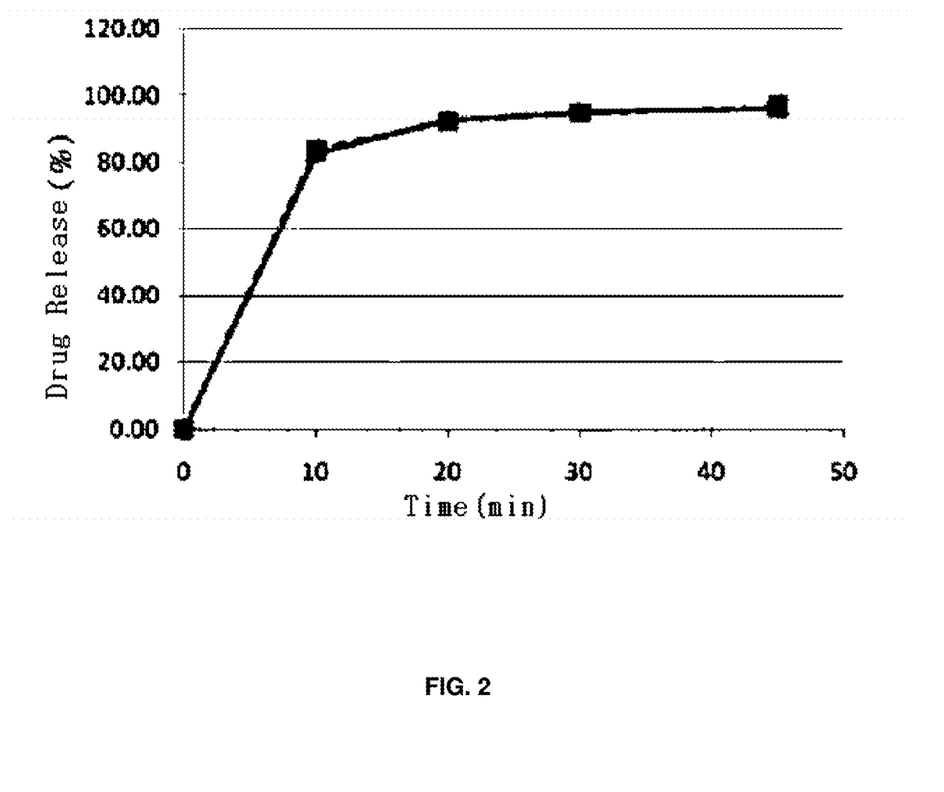
FIG. 2 shows the results of the dissolution test of the solid dispersion-containing tablet obtained in Example 7.
Figure 3:
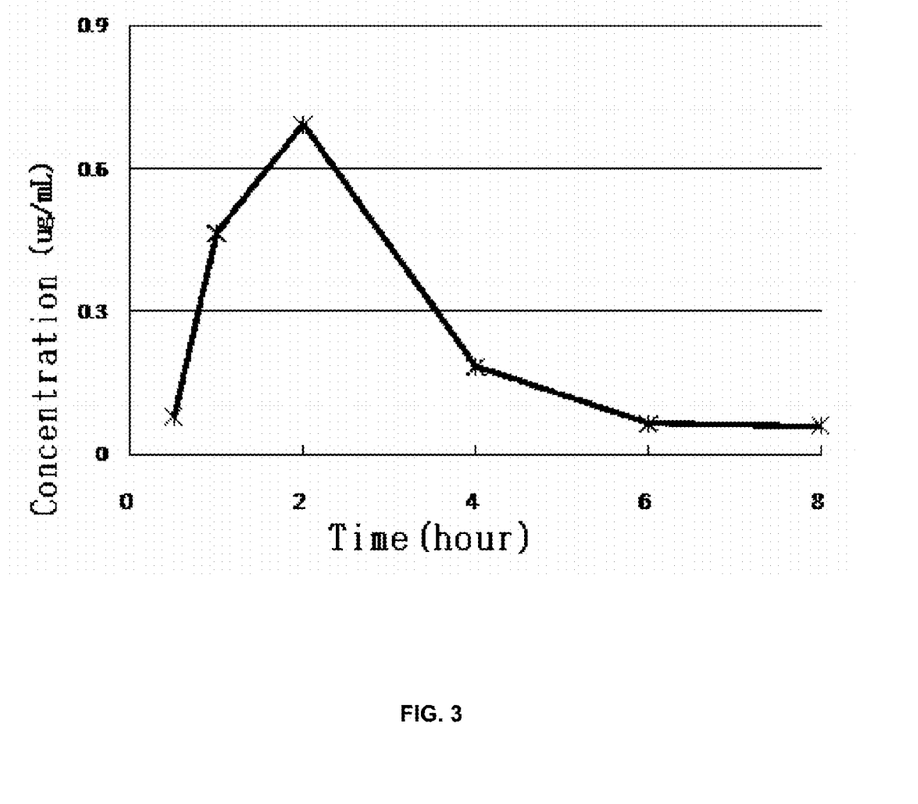
FIG. 3 shows the pharmacokinetic profile observed after the solid dispersion of the present invention is orally administered to a Beagle dog.

The solid dispersion-containing tablet obtained in Example 7 was subjected to a dissolution test according to the second method of United States Pharmacopoeia Dissolution Test (a paddle method) as follows and the results are shown in FIG. 2.

[Dissolution Test]

Method: The second method of United States Pharmacopoeia Dissolution Test (a paddle method)

Dissolution media: 1.5% sodium lauryl sulfate (SLS)-containing distilled water 500 mL Stirring speed: 50 rpm Temperature of eluent: 37±0.5° C.

As can be seen from FIG. 2, the tablet prepared from the solid dispersion of the present invention shows a dissolution rate that satisfies the criteria of Dissolution Test of Tablet—i.e., 80% or more dissolution for 45 min. From this result, it can be confirmed that the dissolution characteristic of the highly insoluble CBI has been improved very effectively.

Experiment 4

Pharmacokinetic Test of the Solid Dispersion for a Beagle Dog

Just before the test, three Beagle dogs were weighed respectively. The solid dispersion of Example 3 as the test group and CBI powder as the control group each weighed in the amount corresponding to 40 mg/kg, were filled into a gelatin capsule and then orally administered. Just before and at 0.5, 1, 2, 4, 6, 8 and 24 h after administration, the blood was collected from the popliteal vein. The plasma was separated from the blood sample by centrifugation and stored/kept at −20° C. until analysis thereof. For the analysis, the plasma sample (0.5 ml) was correctly transferred to a 1.5 ml polypropylene centrifuge tube. This mixture was vortexed for 30 sec and centrifuged at 400 rpm for 10 min. The concentration of CBI in the plasma was analyzed by LCMS/MS. As the mobile phase, a mixed solution of 0.1% formic acid-acetonitrile/deionized water (60/40, v/v), as the flow rate 0.25 mL/min, and as the column Xterr®S C18 (3.0×50 mm, 2.5 micrometer, Waters, USA) were used. The peak was detected by MRM (multiple reaction monitoring) method using triple-quadrupole mass spectrometry. The ionization was analyzed in the positive mode by using electrospray ionization (ESI) wherein the ion spray temperature was set up at 500° C. In the MRM method, the protonated molecular ions of CBI and the internal standard compound were monitored to have the m/z values of 325.1 and 268.0, and the product ions thus produced were monitored to have the m/z values of 91.0 and 155.0, respectively. The area under the concentration-time curve (AUC) of the drug in the plasma was calculated by the linear trapezoidal method. The results are shown in the following Table 13 and FIG. 3.

TABLE 13

| Time (hours) | Blood CBI Concentration (μg/mL) | |
| --- | --- | --- |
| | Test Group | Control Group |
| 0 | 0.0 ± 0.0 | Below the Sensitivity for Quantification |
| 0.5 | 0.080 ± 0.06 | |
| 1 | 0.464 ± 0.28 | |
| 2 | 0.692 ± 0.33 | |
| 4 | 0.183 ± 0.10 | |
| 6 | 0.065 ± 0.04 | |
| 8 | 0.059 ± 0.05 | |
| 24 | Not Detected | |
| AUClast (μg*hr/mL) | 1.98 ± 0.96 | |
| AUCInf (μg*hr/mL) | 2.14 ± 1.04 | |

As can be seen from the above results, the control group to which CBI powder was administered shows the result of "below the sensitivity for quantification" in all the time zones, which confirms that the drug was not orally absorbed at all. On the contrary, the test group to which the solid dispersion of the present invention was administered shows the maximum blood concentration of 0.531 μg/mL at 1 h after administration, which confirms that the absorption by oral administration and bioavailability of CBI have been conspicuously improved.

What is claimed is:

1. A solid dispersion, comprising:
    10 to 50 wt % carbamic acid 3-(4-benzyloxy-phenyl)-isoxazol-5-ylmethyl ester, or a pharmaceutically acceptable salt thereof,
    45 to 85 wt % water-soluble polymer having a glass transition temperature lower than the melting point of carbamic acid 3-(4-benzyloxy-phenyl)-isoxazol-5-ylmethyl ester, and
    1 to 5 wt % plasticizer,
    wherein the solid dispersion is prepared by melt extrusion,
    wherein the water-soluble polymer is selected from polyvinylpyrrolidone, hypromellose acetate succinate and a combination thereof, and
    wherein the plasticizer is selected from the group consisting of D-alpha-tocopheryl polyethylene glycol 1000 succinate, polyethylene glycol 400, and a combination thereof.

2. The solid dispersion of claim 1, wherein the water-soluble polymer is contained in the amount of about 70 to 85 wt % based on the total weight of the composition.

3. The solid dispersion of claim 1, wherein the plasticizer is contained in the amount of with about 1 wt % based on the total weight of the composition.

4. The solid dispersion of claim 1, which comprises 50 to 85 wt % of polyvinylpyrrolidone.

5. The solid dispersion of claim 1, which comprises:
    about 30 wt % of carbamic acid 3-(4-benzyloxy-phenyl)-isoxazol-5-ylmethyl ester,
    about 69 wt % of polyvinylpyrrolidone, and
    about 1 wt % of D-alpha-tocopheryl polyethylene glycol 1000 succinate.

6. The solid dispersion of claim 1, which comprises:
    about 30 wt % of carbamic acid 3-(4-benzyloxy-phenyl)-isoxazol-5-ylmethyl ester,
    about 69 wt % of polyvinylpyrrolidone, and
    about 1 wt % of polyethylene glycol 400.

7. The solid dispersion of claim 1, which comprises:
    about 15 wt % of carbamic acid 3-(4-benzyloxy-phenyl)-isoxazol-5-ylmethyl ester,
    about 84 wt % of hypromellose acetate succinate, and
    about 1 wt % of polyethylene glycol 400.

8. The solid dispersion of claim 1, which melts at a temperature lower than the melting point of carbamic acid 3-(4-benzyloxy-phenyl)-isoxazol-5-ylmethyl ester.

9. An oral composition comprising the solid dispersion of claim 1.

* * * * *